United States Patent
Izaguirre

(10) Patent No.: US 10,427,502 B1
(45) Date of Patent: Oct. 1, 2019

(54) VEHICLE AIR FRESHENER MODULE

(71) Applicant: Armando Izaguirre, Orlando, FL (US)

(72) Inventor: Armando Izaguirre, Orlando, FL (US)

( * ) Notice: Subject to any disclaimer, the term of this patent is extended or adjusted under 35 U.S.C. 154(b) by 503 days.

(21) Appl. No.: 14/989,877

(22) Filed: Jan. 7, 2016

Related U.S. Application Data

(60) Provisional application No. 62/101,843, filed on Jan. 9, 2015.

(51) Int. Cl.
*B60H 3/00* (2006.01)
*A61L 9/12* (2006.01)

(52) U.S. Cl.
CPC .............. *B60H 3/0007* (2013.01); *A61L 9/12* (2013.01); *B60H 3/0014* (2013.01); *B60H 3/0028* (2013.01)

(58) Field of Classification Search
CPC . B60H 3/06; B60H 1/34; B01D 46/10; B01D 46/44; B01D 46/46; F24F 13/00; F24F 13/28; F16K 7/00; F16K 7/10; G05D 23/19
USPC ................... 454/155, 156–158; 55/422, 480; 236/46 R
See application file for complete search history.

(56) References Cited

U.S. PATENT DOCUMENTS

| | | | | |
|---|---|---|---|---|
| 2,575,499 A | * | 11/1951 | Manow | B01D 46/10 454/284 |
| 3,259,050 A | * | 7/1966 | Grimm, III | B60H 3/0007 239/274 |
| 4,067,692 A | * | 1/1978 | Farris | A61L 9/122 422/124 |
| 4,523,870 A | | 6/1985 | Spector | |
| 4,545,524 A | * | 10/1985 | Zelczer | G05D 23/1934 165/217 |
| 4,722,264 A | * | 2/1988 | DeGuisseppe | B60H 3/0007 261/60 |
| 4,925,468 A | * | 5/1990 | Kishi | B01D 46/0006 55/467 |
| 5,071,621 A | | 12/1991 | Tokuhiro et al. | |
| 5,171,485 A | * | 12/1992 | Ryan | A61L 9/03 261/27 |
| 5,269,723 A | | 12/1993 | Bender | |

(Continued)

FOREIGN PATENT DOCUMENTS

KR 20120067599 6/2012

*Primary Examiner* — Gregory L Huson
*Assistant Examiner* — Frances F. Hamilton
(74) *Attorney, Agent, or Firm* — John Rizvi; The Patent Professor®

(57) ABSTRACT

An air freshener module is installed in a compartment slot formed in the dashboard of a vehicle. The module includes a body having a front section and a rear section. The rear section has an air inlet port that is adapted for coupling to the vehicle AC tube. The front section defines a plenum or interior housing space configured to receive an air freshener receptacle or holder that is movable between an open state and a closed state. The front end of the interior housing space defines an air outlet port. An air passageway extends between the air inlet port and the air outlet port. During operation, air admitted through the air inlet port is vented into the interior housing spaced occupied by the air freshener holder, enabling air to pass through an air freshener element and thereby communicate odorized air into the cabin. An adjustable closure regulates the amount of air delivered into the plenum.

7 Claims, 7 Drawing Sheets

(56) References Cited

U.S. PATENT DOCUMENTS

| | | | |
|---|---|---|---|
| 5,370,576 A * | 12/1994 | Krofchalk | B60H 1/00464 |
| | | | 454/143 |
| 5,429,180 A * | 7/1995 | Nishino | A61L 9/12 |
| | | | 165/41 |
| 6,019,676 A * | 2/2000 | Kim | B60H 3/0608 |
| | | | 454/155 |
| 6,030,427 A * | 2/2000 | Sorice | B01D 46/0004 |
| | | | 55/480 |
| 6,581,915 B2 | 6/2003 | Bartsch et al. | |
| 6,623,350 B2 * | 9/2003 | Goupil, Jr. | B60H 3/0616 |
| | | | 454/158 |
| 6,877,674 B2 * | 4/2005 | Choquet | A61L 9/12 |
| | | | 239/34 |
| 7,097,555 B2 * | 8/2006 | Bourbon | B60H 1/34 |
| | | | 422/123 |
| 7,160,515 B2 | 1/2007 | Murdell et al. | |
| 7,997,964 B2 * | 8/2011 | Gehring | B60H 1/345 |
| | | | 454/152 |
| 8,170,405 B2 | 5/2012 | Harris | |
| 8,931,712 B2 * | 1/2015 | Nagano | A61L 9/12 |
| | | | 165/202 |
| 2003/0186643 A1 * | 10/2003 | Feuillard | A61L 9/122 |
| | | | 454/157 |
| 2003/0206832 A1 | 11/2003 | Chiao | |
| 2004/0072532 A1 * | 4/2004 | Cho | B60H 1/3414 |
| | | | 454/155 |
| 2004/0072533 A1 * | 4/2004 | Cho | B60H 1/3414 |
| | | | 454/155 |
| 2005/0167860 A1 | 8/2005 | Brooks | |
| 2014/0250654 A1 * | 9/2014 | Forest | B60H 1/243 |
| | | | 29/402.08 |

\* cited by examiner

VEHICLE AIR FRESHENER MODULE

CROSS-REFERENCE TO RELATED APPLICATION

This application claims the benefit of U.S. Provisional Patent Application Ser. No. 62/101,843, filed Jan. 9, 2015, which is incorporated herein in its entirety.

FIELD OF THE INVENTION

The present invention relates to a device for deodorizing a vehicle, and more particularly, to an onboard vehicle air freshener module that is adapted for connection to an air tube of the vehicle AC system.

BACKGROUND OF THE INVENTION

The interior cabin space of vehicles is typically ventilated by air circulating through the open windows. This natural air approach can be effective on some occasions, but is not a universal solution under all driving conditions. If there is inclement weather, such as a rainy or cold day, the windows will need to remain closed. Even when the weather is more amenable, it can be difficult to precisely regulate the quality of the ventilation activity. A proper ventilation system enables the control of factors such as the rate of air flow and the temperature of the incoming air. However, it is difficult to manage these parameters when the ventilation depends on ambient air entering through windows.

As an alternative to the natural air flow afforded by open windows, automobiles are equipped with heating, ventilation, and air conditioning (HVAC) systems that allow an occupant to control the temperature and flow of air communicating through various tubes and vents into the cabin interior. The HVAC system facilitates a climate control of the vehicle interior that can operate regardless of the weather conditions exterior to the vehicle.

Even though vehicle HVAC systems offer improved ventilation capabilities over an approach relying upon air entering through the windows, both types of ventilation approaches fail to provide any odorizing activity. This problem raises additional concerns when it is necessary to odorize the cabin space in order to ameliorate or counteract any foul odors present in the cabin. This might occur, for example, in vehicles where persistent odors from mold and bacteria are present. The HVAC system, in fact, can be a troublesome source of mold because of the build-up of condensate that can occur through the normal operation of the air conditioning system, specifically during the release of moisture from humid air that attends the reduction in air temperature of an air conditioning operation. This condensate, if not properly removed, can stagnate and form foul-smelling mold within the ventilation passageways. This odor is then conveyed by the forced air stream into the cabin space. It is very difficult to clean the HVAC air passageways and remove all traces of mold since access to the air tubes is very limited. The HVAC system and accompanying air tubes are housed within the dashboard and not readily accessible, except for a complex service operation that removes the dash components. Due to the challenges in maintaining the air vents in a dry and moisture-free state, the HVAC system is vulnerable to mold build-up, especially in humid climates.

One way to odorize the vehicle cabin area involves the use of deodorizing elements that emanate a certain pleasant scent. These air freshener elements come in a variety of forms, such as a freshener stick that is located somewhere in the cabin area, like atop the dashboard. In one configuration, the freshener element is placed in a location where it is exposed to the ambient air flow that prevails in the cabin space. In this arrangement, the effectiveness of the freshener element depends in some degree on the amount of air flow that contacts the element. In another configuration, the freshener element is attached to the outside of the air vent, so that forced air emerging from the vent will contact the freshener element and actively facilitate an odorizing activity. However, it can be cumbersome or difficult to attach the air freshener element to the vent, especially if the vent and freshener element are not well adapted for integration with each other. In addition, such air fresheners often become loose and fall off the air vent, distracting the driver and potentially causing a safety hazard for the driver, passenger(s) and other vehicles.

Accordingly, there remains a need in the art for a safe and efficient means to odorize the vehicle cabin environment.

SUMMARY OF THE INVENTION

The present invention overcomes the deficiencies of the known art and the problems that remain unsolved by providing an onboard vehicle air freshener module that is adapted for connection to an air tube of the vehicle AC system, for deodorizing the air space in the vehicle cabin environment. The vehicle air freshener module is configured to be inserted and integrated within a vehicle dashboard or any other part of the passenger compartment, providing passenger compartment freshening while minimizing the risk of distracting the driver.

In a first implementation of the invention, an air freshener module comprises a body including a shell having at least opposing sidewalls and defining an interior space. The shell defines an air inlet at a rear of the body and an air outlet at the front of the body. The interior space defines an air passageway extending between the air inlet and the air outlet. At least one valve is configured to control the passage of air between the air inlet and the air outlet and is selectively operable between an open position and a closed position. A receptacle defining at least one compartment to hold an air freshener element is disposed in the air outlet and is movable with respect to the body between an open position for access to an interior of the receptacle from outside the body, and a closed position preventing access to the interior of the receptacle from outside the body.

In another aspect, the receptacle can define a plurality of openings therethrough for permitting the flow of air therethrough from the passageway to outside the body when the receptacle is in the closed position.

In still another aspect, the receptacle can include at least a front panel, a rear panel, and a mid panel interposed between the front panel and the rear panel. The mid panel divides the at least one compartment into a front compartment and a rear compartment.

In yet another aspect, the front compartment can be smaller than the rear compartment.

In a still further aspect, the front panel and the mid panel can be substantially parallel one with the other.

In another aspect, a top edge of the mid panel can be more proximate to the front panel than to the rear panel.

In another aspect, the receptacle can be slidable with respect to the body and can slidably adopt a closed position in which the front panel is substantially flush with a most forward surface of the body and an open position in which the front panel extends forward of the most forward surface of the body for access to the at least one compartment.

In a still further aspect, the receptacle can be pivotal with respect to the body.

In yet another aspect, the receptacle can pivot about an axis substantially parallel to and substantially at a bottom edge of the front panel.

In another aspect, the receptacle can be selectively and reversibly removed from the body and reattached to the body.

In still another aspect, the body can define opposing indents formed in the opposing sidewalls of the body along the axis and the receptacle can include a projection on each side thereof. Each projection is received in one of the indents and is pivotal therein.

In yet another aspect, the valve can include a throttle plate disposed in the air passageway proximate to the air inlet. The throttle plate can be is pivotal with respect to the body between an open position and a closed position.

In another aspect, the throttle plate can pivot about an axis substantially orthogonal to a longitudinal axis of the air passageway.

In still another aspect, the air freshener module can further include a user control switch operably connected to the closure mechanism for selectively moving the closure mechanism between the open position and the closed position.

In yet another aspect, an air freshener module comprises a body including a shell having at least opposing sidewalls and defining an interior space. The shell defines an air inlet at a rear of the body and an air outlet at the front of the body. The interior space defines an air passageway extending between the air inlet and the air outlet. At least one valve is configured to control the passage of air between the air inlet and the air outlet and comprises a throttle plate disposed in the air passageway proximate to the air inlet and selectively pivotal with respect to the body between an open position and a closed position. A receptacle has a front panel, a rear panel, and a mid panel interposed between the front panel and the rear panel. The mid panel is substantially parallel to the front panel and defines in combination with the front panel and the rear panel a front compartment and a rear compartment for holding an air freshener element. The receptacle is disposed in the air outlet and is movable with respect to the body between an open position for access to the front compartment and rear compartment of the receptacle from outside the body, and a closed position preventing access to the front compartment and the rear compartment of the receptacle from outside the body.

In yet another aspect, an air freshener module comprises a body including a shell having at least opposing sidewalls and defining an interior space. The shell defines an air inlet at a rear of the body and an air outlet at the front of the body. The interior space defines an air passageway extending between the air inlet and the air outlet. At least one valve is configured to control the passage of air between the air inlet and the air outlet and comprises a throttle plate disposed in the air passageway proximate to the air inlet and is selectively pivotal with respect to the body between an open position and a closed position. A user control switch is operably connected to the throttle plate for selectively pivoting the throttle plate between the open position and the closed position. A receptacle has a front panel and a rear panel. The front panel and the rear panel delimit at least one compartment therebetween to hold an air freshener element. The receptacle is disposed in the air outlet and is movable with respect to the body between an open position for access to the at least one compartment of the receptacle from outside the body, and a closed position preventing access to the at least one compartment from outside the body.

These and other aspects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, in which.

Like reference numerals refer to like parts throughout the several views of the drawings.

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall be used to describe the invention in accordance with their common meaning. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Figure 1:
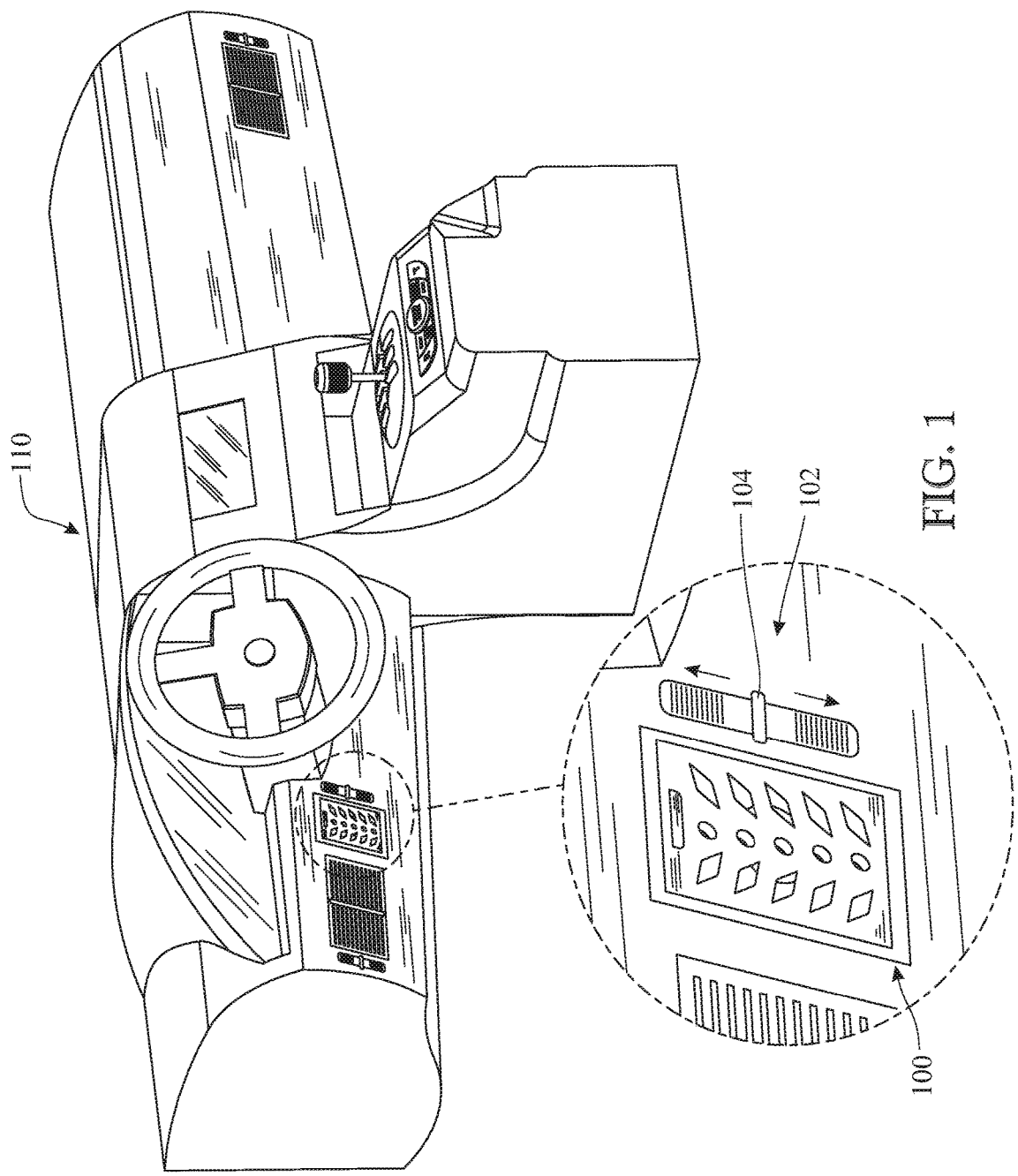
FIG. 1 presents an isometric view of an exemplary vehicle air freshener module in accordance with a first embodiment of the invention, demonstrating installation of the module in an exemplary vehicle dashboard.
Figure 2:
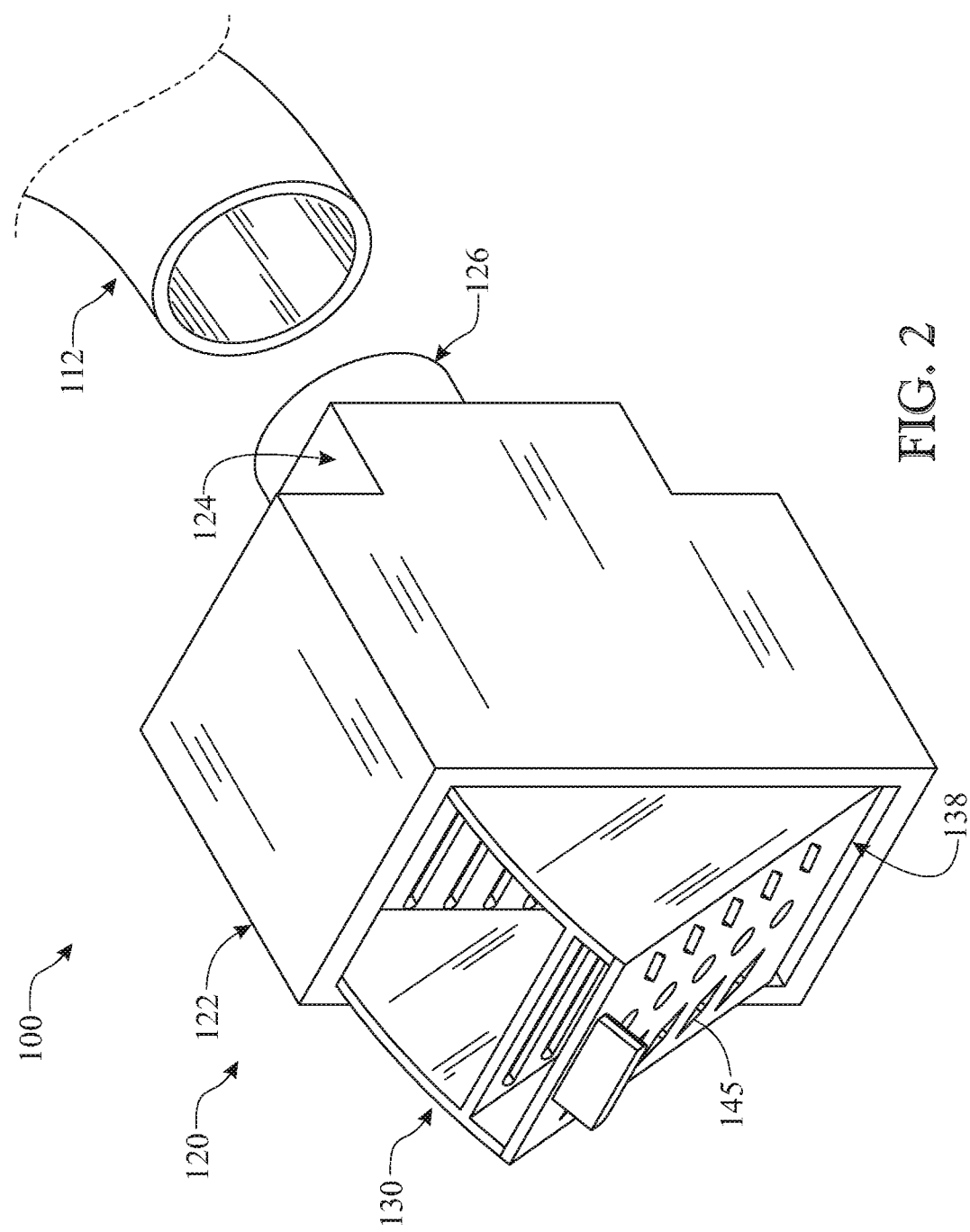
FIG. 2 presents an isometric front view of the vehicle air freshener module originally introduced in FIG. 1, showing the module in its assembled form having a pivoting air freshener holder configured in an open state and depicting the module in an exploded view relative to a connecting vehicle AC tube.

A vehicle air freshener module 100 is presented in various configurations in the illustrations of FIGS. 1 through 5, according to a first embodiment of the invention. The illustration of FIG. 1 shows the air freshener module 100 installed in the dashboard 110 of a vehicle, such as in an area proximate to the steering wheel to permit ready access by the driver. As shown in FIG. 2, the air freshener module 100 is adapted for fluid connection to an air passageway or tube 112 of the vehicle air conditioning (AC) system. The air freshener module 100 vents air conveyed by the AC system through an air freshening element housed in the air freshener module 100 and then vents the scented air into the vehicle cabin space, thereby odorizing the ambient cabin air. As shown in FIG. 1, the air freshener module 100 is equipped with an air control panel 102 having a user control switch 104 that regulates the amount of air vented through air freshener module 100.

As shown in FIGS. 2 through 5, the air freshener module 100 of the present embodiment includes a casing or body 120 having a front section 122, a mid section 124, and a rear section 126. The mid section 124 is disposed between and contiguous with the front section 122 and the rear section 126. The front section 122 defines an interior space or cavity 160 (FIG. 4) having a front opening that defines an air outlet end 138 of body 120. The air outlet end 138 faces towards the vehicle cabin during installation of the air freshener module 100. The rear section 126 defines an interior cavity 164 having an opening that defines an air inlet end 136 of body 120. The mid section 124 defines an interior cavity 162 that is contiguous with the interior cavity 160 of front section 122 and the interior cavity 164 of rear section 126.

Each one of the front section 122, the mid section 124, and the rear section 126 is open-ended. This open-ended contiguous arrangement among the front section 122, the mid section 124, and the rear section 126 defines an airway or air passageway 166 extending between the air inlet end 136 at rear section 126 and the air outlet end 138 at the front section 122 of the body 120. The air passageway 166 extends generally along a longitudinal dimension of body 120. The front section 122, the mid section 124, and the rear section 126 of the present embodiment cooperatively form an integral, unified, single-body construction of body 120.

The front section 122 depicted herein has a hollow-body construction in the form of a generally shell-type structure. The shell-type structure includes an axially-extending, outer peripheral sidewall 170 having an upper end 171 and a lower end 172. The outer peripheral sidewall 170 extends in a generally axial or longitudinal direction. The front section 122 further includes a radially-extending, back sidewall 173 that extends radially inward (with respect to a central longitudinal axis 128) from the outer peripheral sidewall 170. The combination of the outer peripheral sidewall 170 and the back sidewall 173 cooperatively defines the interior cavity 160 of the front section 122.

Similarly, the mid section 124 of body 120 has a hollow-body construction in the form of a generally shell-type structure. The mid section 124 is contiguous with the front section 122 at the back sidewall 173 of the front section 122. The interior cavity 162 defined by the mid section 124 has a transverse dimension that is smaller than the interior cavity 160 defined by the front section 122. The mid section 124 includes a radially-extending back surface 175.

Figure 4:
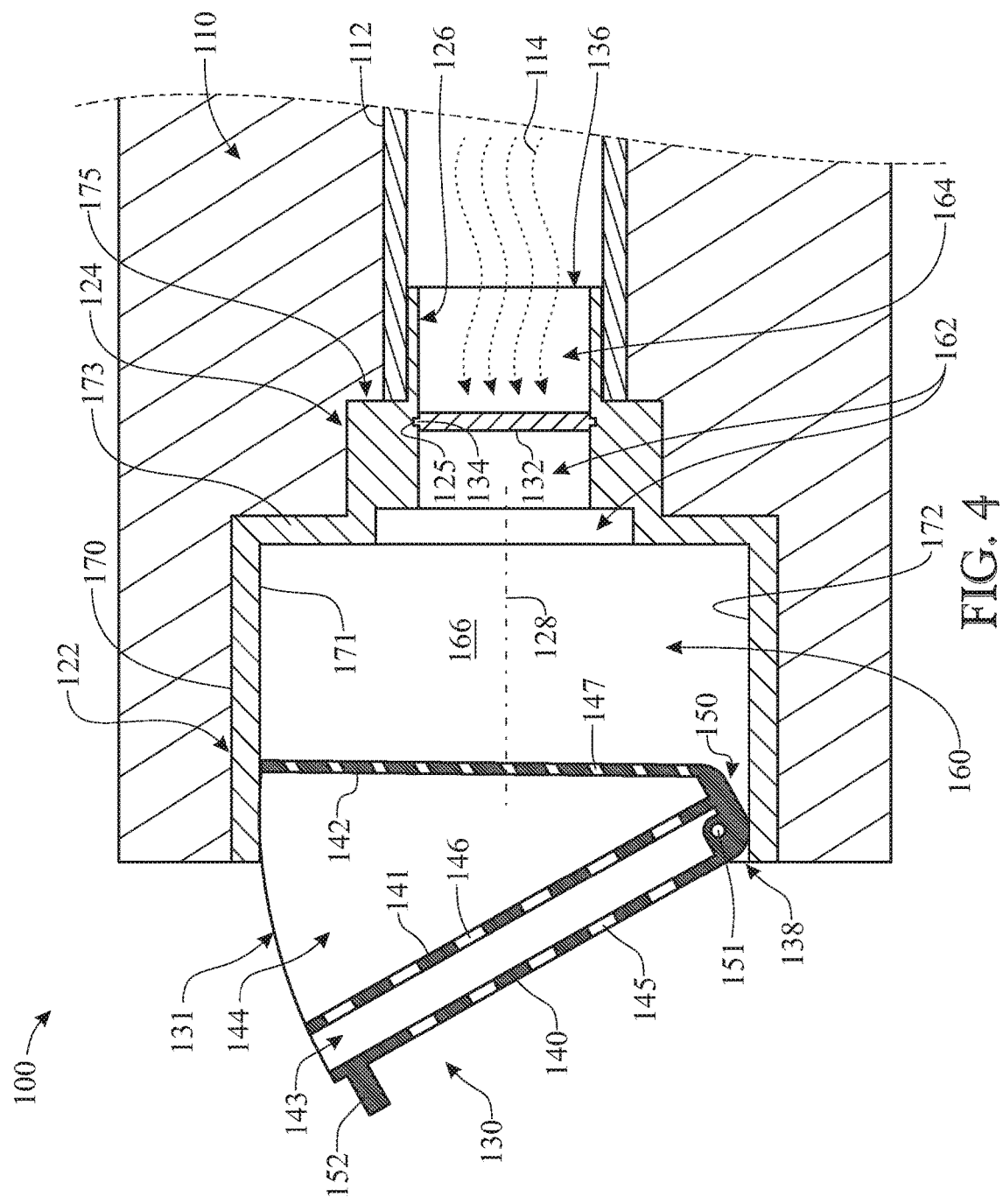
FIG. 4 presents a cross-sectional side elevation view of the vehicle air freshener module originally introduced in FIG. 1, showing the module as installed in the vehicle dashboard and configured in an air-blocking state to block the ingress of air and further configured with the pivoting air freshener holder in an open state.

During installation, as best shown in FIG. 4, the air freshener module 100 is arranged so that the tubular rear section 126 slidingly fits into the air tube 112. The advancement or insertion of the rear section 126 into the air tube 112 is complete when the air tube 112 abuts against the back surface 175 of the mid section 124. The rear section 126 of the body 120 of the present embodiment has a generally tubular construction that is appropriately sized and dimensioned to fit within the air tube 112 of the vehicle AC system in a frictional male-female fashion during installation. This frictional male-female interfit arrangement provides a suitable air-tight coupling between the air freshener module 100 and the air tube 112 that facilitates the transfer of fresh air from the air tube 112 into the air freshener module 100 via the air inlet end 136 at the rear section 126. The interior cavity 164 defined by the rear section 126 of the present embodiment has a transverse dimension that is generally coextensive with the interior cavity 162 defined by the mid section 124.

Figure 5:
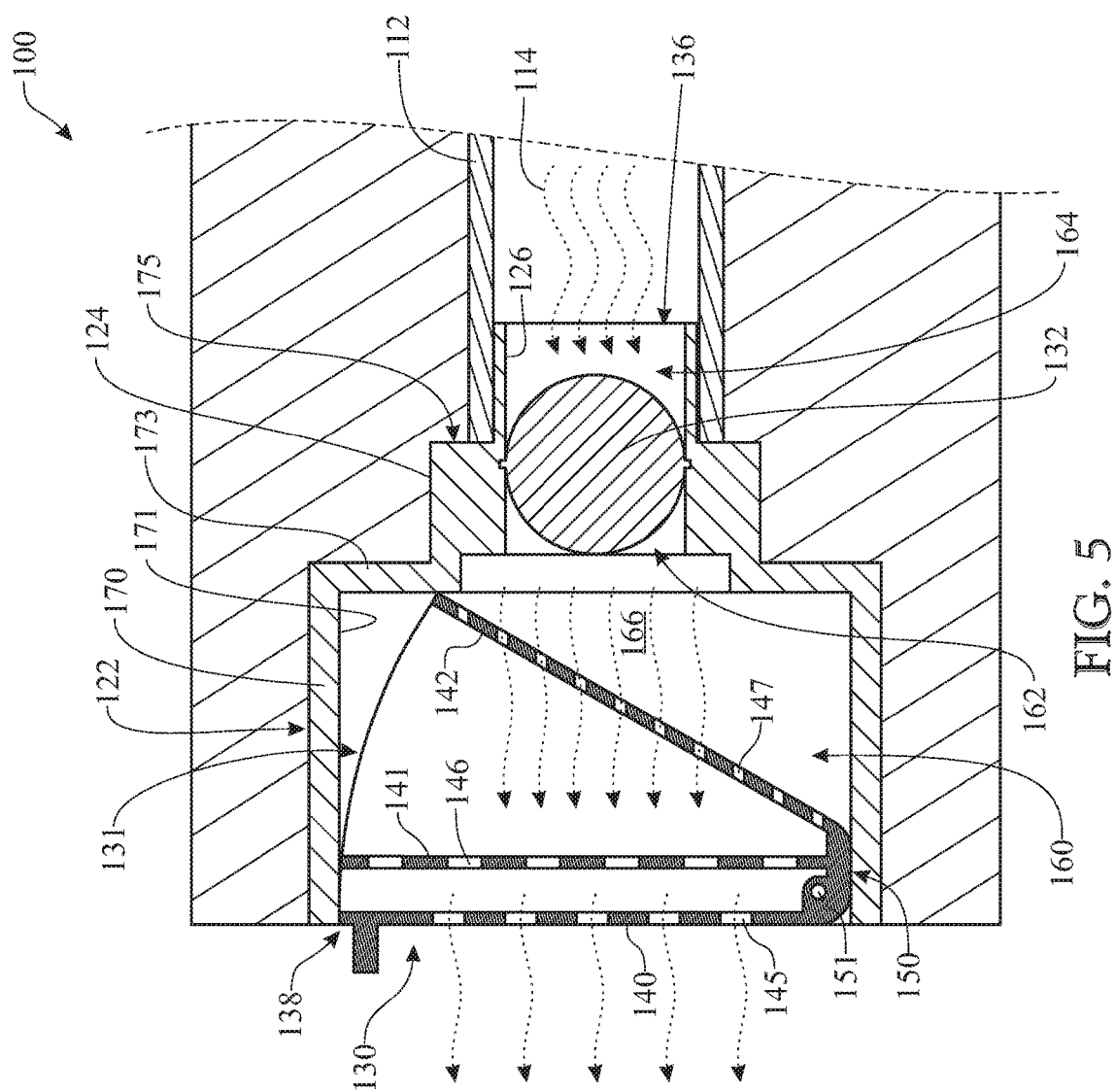
FIG. 5 presents a cross-sectional side elevation view of the vehicle air freshener module originally introduced in FIG. 1, showing the module as installed in the vehicle dashboard and configured in an air-passing state to permit the ingress of air and further configured with the air freshener holder in a closed state.

The air freshener module 100 further includes a movable air freshener receptacle or holder 130. The air freshener holder 130 is housed during assembly in the interior cavity 160 of front section 122. The air freshener holder 130 of the depicted embodiment is a removable component. In its assembled position, the air freshener holder 130 is configured in a pivotable relationship within the body 120, and more specifically with the front section 122 of the body 120. The air freshener holder 130 can pivot between a fully open position (FIG. 4) and a fully closed position (FIG. 5). The front section 122 of the body 120 is suitably sized and configured to facilitate the assembled placement of air freshener holder 130 within the interior cavity 160 and to accommodate the full range of operative pivoting motion of air freshener holder 130. The air freshener holder 130 is configured to hold, contain, or otherwise house an air freshener element.

Figure 3:
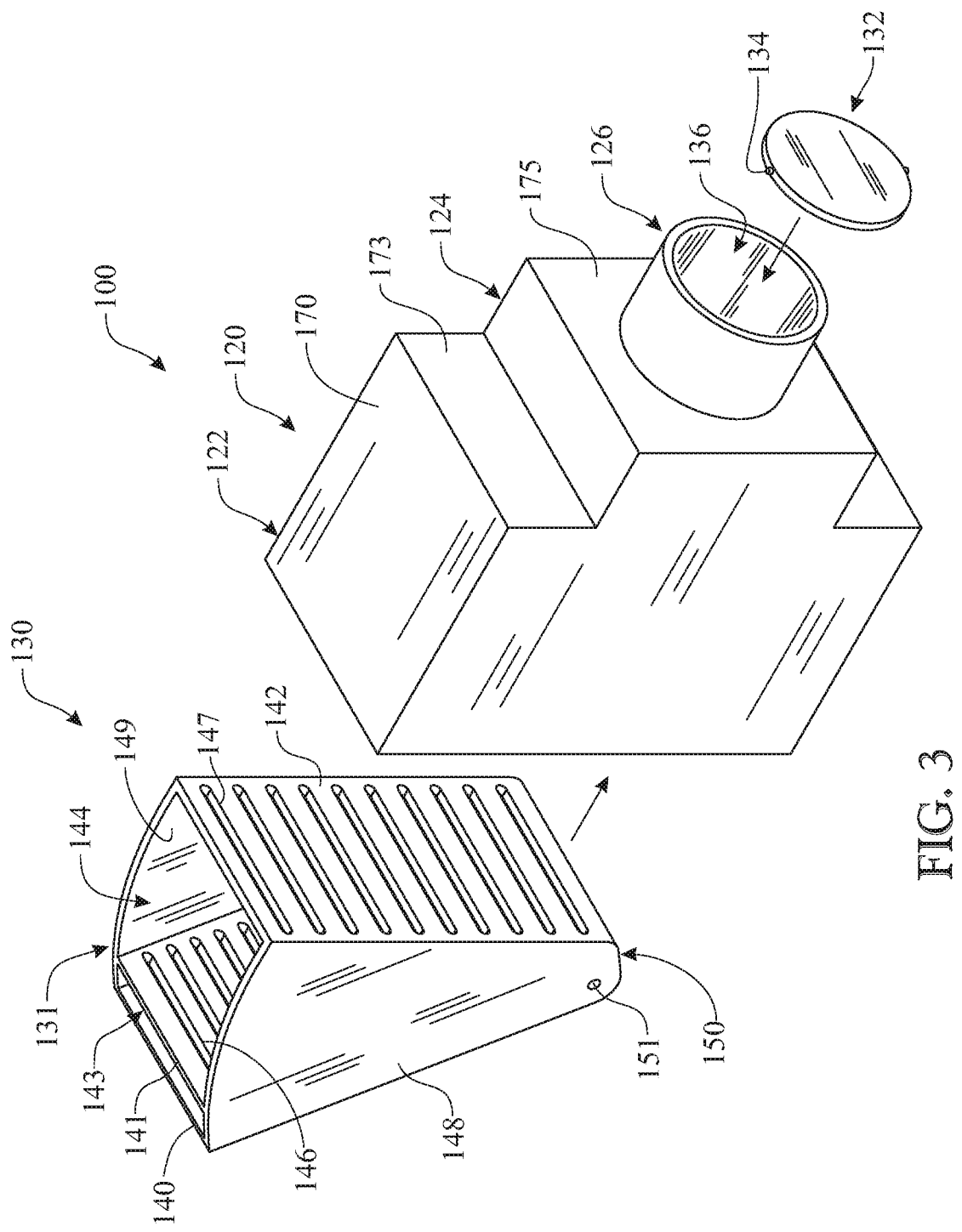
FIG. 3 presents an isometric rear exploded view of the vehicle air freshener module originally introduced in FIG. 1.

The air freshener holder 130 of the present embodiment has an enclosed, generally V-shaped configuration including a front panel 140, a partition or mid panel 141, a rear panel 142, and a pair of sidewalls 148 and 149, as best shown in FIG. 3. The front panel 140 defines the front end of air freshener holder 130, while the rear panel 142 defines the back end of air freshener holder 130. The front panel 140 is disposed in a spaced-apart, opposing, generally parallel relationship with the mid panel 141. The rear panel 142 is disposed in a spaced-apart, opposing, angled relationship with the mid panel 141. The air freshener holder 130 has an open, wide-mouth top 131 and a relatively narrow bottom end 150. The air freshener holder 130 is open at the top 131 and closed at the bottom end 150. The rear panel 142 angles away from the mid panel 141 as it extends away from the bottom end 150. Each one of the front panel 140, mid panel 141, and rear panel 142 has a generally planar construction.

The air freshener holder 130 includes a front compartment 143 that is defined between the front panel 140 and the mid panel 141. The front compartment 143 of the present embodiment is uniformly sized and has a generally flat-shaped, slot-shaped or planar construction that is suited to house a generally flat air freshener cartridge. This type of air freshener fits snugly within the front compartment 143 and resists excessive movement in response to airflow passing through the air freshener, which could cause a disturbing rattle. The air freshener holder 130 further includes a rear compartment 144 that is defined between the mid panel 141 and the rear panel 142. The rear compartment 144 of the present embodiment has a generally wedge-shaped construction that is comparatively larger than the front compartment 143. The rear compartment 144 becomes progressively wider moving in the direction from the bottom end 150 to the open top 131. The construction and geometry of the rear compartment 144 are suited to house a bulky or non-planar air freshener cartridge. The wedge-shaped rear compartment 144 can accommodate air freshener cartridges of varying sizes. The mid panel 141 functions as a partition or divider to create the front compartment 143 and the rear compartment 144.

As shown in FIG. 3, the air freshener holder 130 is provided with a pair of attachment features 151 in the pair of sidewalls 148 and 149 proximate the bottom end 150 of the air freshener holder 130. The attachment features 151 define a pivoting axis of the air freshener holder 130. As shown in the figure, in one exemplary form the attachment features 151 are constituted by a pair of indents formed in sidewalls 148 and 149 that lock or snap into place with corresponding complementary projections that are formed in the front section 122 of the body 120. This interlocking, snap-fit arrangement enables the air freshener holder 130 to pivot or rotate within the front section 122 about the pivoting axis defined by the attachment features 151. The air freshener holder 130 can be removed by releasing or disengaging the snap-fit connection of the indents and complementary projections. During assembly, the air freshener holder 130 is maneuvered into the interior cavity 160 of the front section 122 through the air outlet end 138 and snapped into place via the attachment features 151 (for which the air freshener holder 130 and/or the front section 122 can be slightly deformable and resilient to provide the snapping effect). As shown in FIG. 4, in its assembled location, the air freshener holder 130 can pivotably rest on the lower end 172 of the outer peripheral sidewall 170 of the front section 122. The air freshener holder 130 includes a projection or handle 152 extending from an upper end of front panel 140 to facilitate user movement of air freshener holder 130 through its pivoting orientations.

The air freshener holder 130 is provided with various openings to facilitate the passage of airflow through the air freshener holder 130 and the air freshener cartridge(s) housed in the air freshener holder 130. The airflow occurs successively through the rear panel 142, the mid panel 141, and the front panel 140. In particular, in order to facilitate the communication of air through the air freshener holder 130, the rear panel 142 is provided with a set of slits or openings 147; the mid panel 141 is provided with a set of slits or openings 146; and the front panel 140 is provided with a set of slits or openings 145, as shown in FIGS. 3 through 5. Any type or arrangement or geometry of slits or openings can be used.

The air freshener module 100 further includes a user-operable closure mechanism 132 that controllably regulates the amount of air that is admitted into the interior cavity 160 of the front section 122 for odorizing. The interior cavity 160 of the front section 122 is occupied by the air freshener holder 130 and the air freshener cartridge that it houses (not shown), and so the closure mechanism 132 regulates the amount of air that is odorized by the air freshener contained in air freshener holder 130.

The closure mechanism 132 of the present embodiment is provided in the form of a planar, generally circular, disc-shaped member or throttle plate that is rotatably attached to the body 120 at some point along the air passageway 166, and is rotatable around an axis generally orthogonal to the longitudinal axis of the body 120, to block or unblock air passing through the air passageway 166. For instance, as best shown in FIGS. 3 and 4, the closure mechanism 132 of the present embodiment is located in the interior cavity 162 of the mid section 124. The closure mechanism 132 is generally the same size as the transverse cross-sectional area of the interior cavity 162 of the mid section 124. In this manner, when the closure mechanism 132 is oriented so that its main surface area is generally perpendicular to the longitudinal axis of the body 120, as shown in FIG. 4, the closure mechanism 132 substantially blocks the passage of any airflow entering via the air inlet end 136.

The closure mechanism 132 is fitted with a pair of fastener or attachment projections 134 that are diametrically opposed to one another. During assembly, the closure mechanism 132 is maneuvered into the interior cavity 162 of the mid section 124 and locked into place. In particular, the attachment projections 134 are snap-fit into corresponding complementary indents 125 formed in an axial surface of the mid section 124. This snap-fit connection secures or locks the closure mechanism 132 into an upright pivotable configuration within the interior cavity 162. When the closure mechanism 132 is so assembled into the air freshener module 100, the diametrical transverse axis that extends between the pair of attachment projections 134 of closure mechanism 132 defines a pivot axis for closure mechanism 132. This pivot axis is generally orthogonal to the longitudinal axis of body 120. The air freshener module 100 includes a cable assembly, articulated rod set, or other means for connecting the control switch 104 of air control panel 102 to the closure mechanism 132 in order to permit the user to implement user-selective control of the pivoting movement of closure mechanism 132. In this manner, the user can select the rotational orientation of closure mechanism 132 and so regulate the airflow communicated through the air freshener module 100. Any means known to those skilled in the art can be used to establish this control feature of closure mechanism 132.

The illustrations of FIGS. 4 and 5 depict different operating states or modes of operation of the air freshener module 100. On one hand, FIG. 4 depicts a mode of operation in which the air freshener holder 130 is positioned in an open configuration. This open configuration is suitable for loading the air freshener holder 130 with an air freshener cartridge as part of a preliminary set-up procedure. The air freshener holder 130 can be loaded by placing a single flat cartridge in the front compartment 143, a single bulkier cartridge in the rear compartment 144, or a combination thereof, to name a few examples. In turn, FIG. 5 depicts a mode of operation in which the air freshener holder 130 is positioned in a closed configuration. This closed configuration is suitable for enabling conveyed air moving through the air freshener module 100 to pass through the air freshener holder 130, where the airflow is odorized before exiting into the vehicle cabin.

Referring to FIG. 4, the air freshener holder 130 is pivoted outwards away from the body 120 of air freshener module 100, allowing the user to access both the front compartment 143 and the rear compartment 144 of air freshener holder 130. Depending on the application and the deodorizing requirements, the user inserts or loads the appropriate air freshener cartridge into either the front compartment 143 or the rear compartment 144 of air freshener holder 130. In this cartridge loading mode, there is no need for the communication of airflow through the air freshener module 100. Accordingly, as shown, the closure mechanism 132 is selectively moved or rotated by the user so that the closure mechanism 132 is positioned in a substantially orthogonal orientation to the longitudinal axis of the body 120 of the air freshener module 100. In this closed position, the closure mechanism 132 substantially blocks or restricts the airflow 114 entering via the air inlet end 136 from proceeding past the closure mechanism 132. After the cartridge loading step is complete, the loaded air freshener holder 130 can be pivoted fully back into the module 130 so that it adopts the closed configuration of FIG. 5.

Referring to FIG. 5, the air freshener holder 130 is depicted in a closed state in which the open, wide-mouth top 131 of the air freshener holder 130 is arranged within the interior cavity 160 of the front section 122, and the front panel 140 of the air freshener holder 130 is closing the air outlet end 138 except for the openings 145. In this closed state, the front panel 140 of the air freshener holder 130 is generally flush with the air outlet end 138 of body 120. Additionally, in its operative resting configuration, the air freshener holder 130 is positioned so that its rear panel 142 rests or abuts against an upper portion of the back sidewall 173 of the front section 122, as shown. This abutment helps stabilize the location and positioning of air freshener holder 130. The throttle plate 132 is selectively moved or rotated by the user so that the throttle plate 132 is positioned in a substantially parallel orientation to the longitudinal axis of the body 120, as shown. In this open position, the closure mechanism 132 permits the airflow 114 entering via the air inlet end 136 to continue into the interior cavity 160 of the front section 122 and pass through the air freshener holder 130, as shown.

During operation, fresh airflow 114 conveyed by air tube 112 enters the air freshener module 100 via the air inlet end 136 at the rear section 126. The open throttle plate 132 allows the incoming airflow 114 to continue through the interior cavity 162 of the mid section 124 and proceed into the interior cavity 164 of the front section 122. The airflow 114 travels through the air freshener cartridge(s) (not shown) loaded into the air freshener holder 130 and emerges or exits from the air freshener module 100 via the air outlet end 138, and more specifically, through the openings 145 of the front panel 140. During its passage through the air freshener holder 130, the airflow 114 becomes odorized via its contact with the air freshener cartridge(s). The odorized airflow 114 exits via the front panel openings 145 into the vehicle cabin environment and deodorizes the cabin air space.

Figure 6:
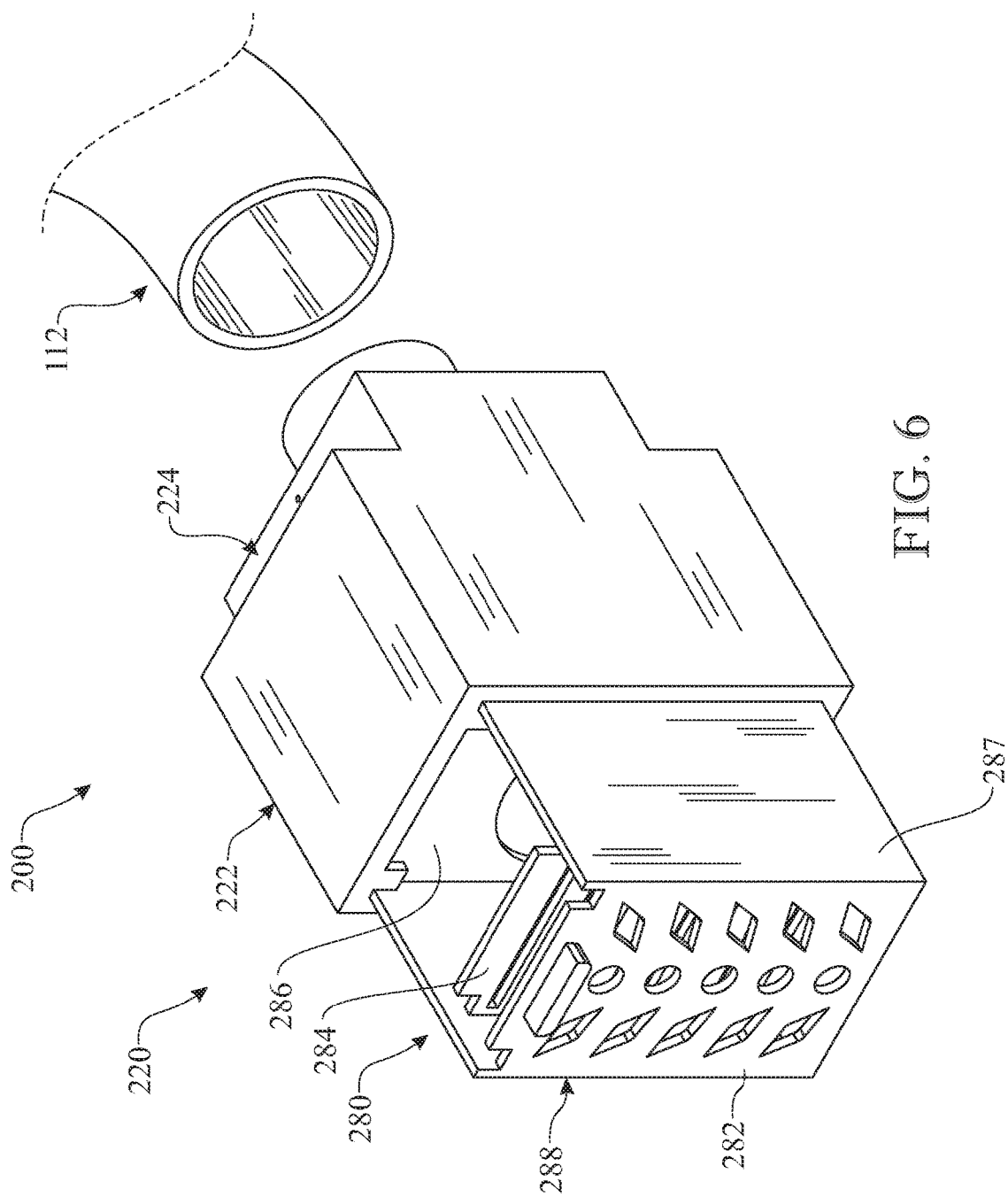
FIG. 6 presents an isometric view of an exemplary vehicle air freshener module in accordance with a second embodiment of the invention, showing the module in its assembled form having a sliding air freshener holder configured in an open state and depicting the module in an exploded view relative to a connecting vehicle AC tube.
Figure 7:
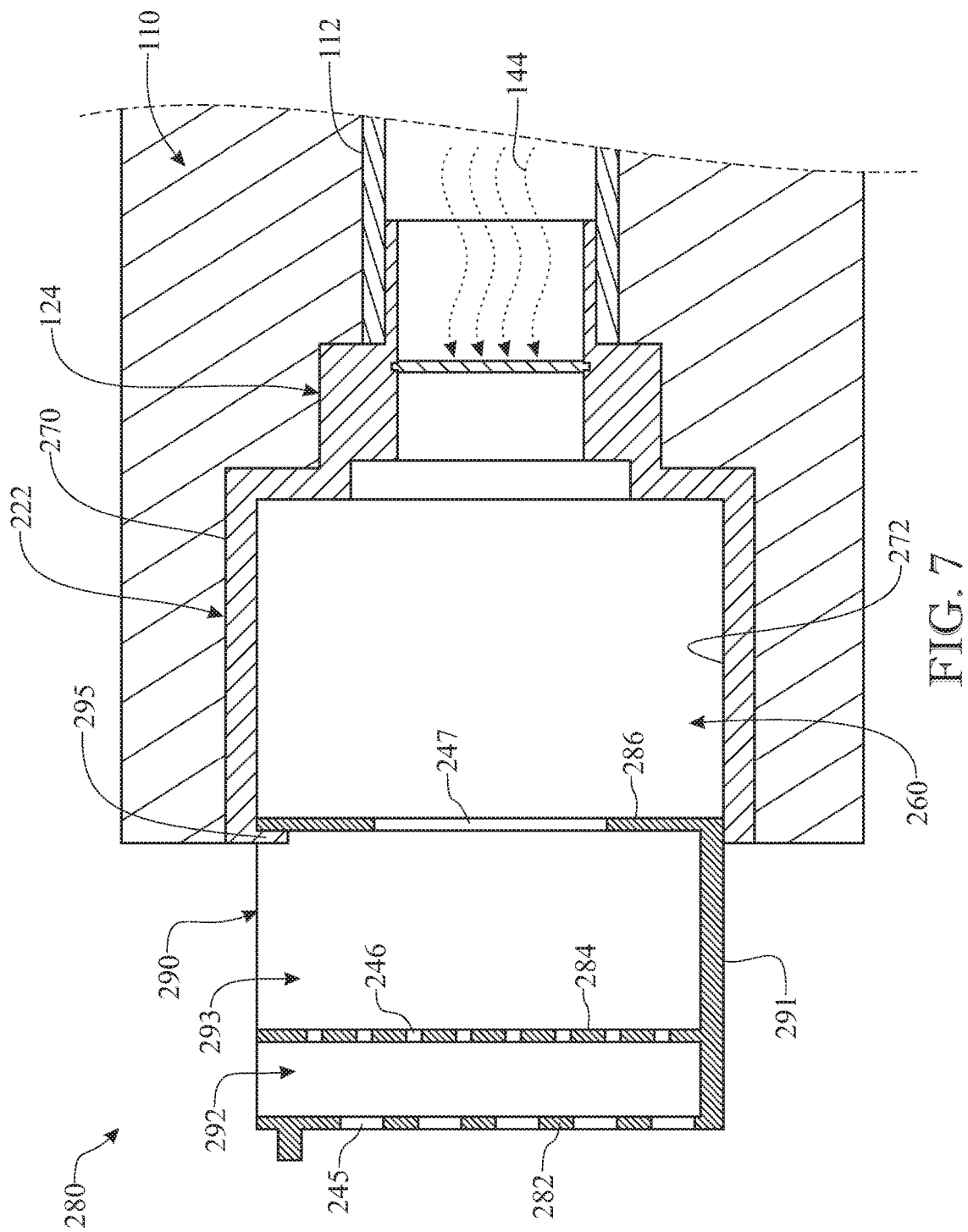
FIG. 7 presents a cross-sectional side elevation view of the vehicle air freshener module originally introduced in FIG. 6, showing the module as installed in the vehicle dashboard and configured in an air-blocking state to block the ingress of air and further configured with the sliding air freshener holder in an open state.

A vehicle air freshener module 200 is presented in various configurations in the illustrations of FIGS. 6 and 7, according to a second embodiment of the invention. Like features of the air freshener module 200 and the air freshener module 100 of FIGS. 1 through 5 are numbered the same except preceded by the numeral '2'. The air freshener module 200 includes a sliding-type air freshener receptacle or holder 280, compared to the pivot-type air freshener receptacle or holder 130 of air freshener module 100 shown in FIGS. 1 through 5.

The air freshener holder 280 is provided in the form of a slidable drawer-type structure having a front panel 282, a divider partition or mid panel 284, a rear panel 286, and a pair of sidewalls 287 and 288. The front panel 282 defines the front end of air freshener holder 280, while the rear panel 286 defines the back end of air freshener holder 280. The front panel 282 is disposed in a spaced-apart, opposing, generally parallel relationship with the mid panel 284. The rear panel 286 is disposed in a spaced-apart, opposing, generally parallel relationship with the mid panel 284. The air freshener holder 280 has an open, wide-mouth top 290 and a flat planar bottom end 291 that is coextensive with the top 290. The air freshener holder 280 is open at the top 290 and closed at the bottom end 291. Each one of the front panel 282, mid panel 284, and rear panel 286 has a generally planar construction.

The air freshener holder 280 includes a front cartridge slot or compartment 292 that is defined between the front panel 282 and the mid panel 284. The front compartment 292 is uniformly sized and has a generally flat-shaped or planar construction that is suited to house a generally flat air freshener cartridge. The air freshener holder 280 further includes a rear cartridge slot or compartment 293 that is defined between the mid panel 284 and the rear panel 286. The rear compartment 293 has a generally rectangular prism construction that is comparatively larger than the front compartment 292. The rear compartment 293 is suited to house a bulky air freshener cartridge. The rear compartment 293 can accommodate air freshener cartridges of varying sizes. The mid panel 284 functions as a partition or divider to create the front cartridge slot 292 and the rear cartridge slot 293.

The air freshener holder 280 is slidably located within the cavity 260 of the front section 222. The air freshener holder 280 is supported at its bottom end 291 by resting on the lower end 272 of the outer peripheral sidewall 270 of front section 222. The air freshener holder 280 can be shifted between various positions by appropriately displacing or sliding the drawer-type air freshener holder 280. The illustration of FIG. 7 depicts an open, cartridge-loading access configuration in which the air freshener holder 280 is withdrawn from air freshener module 200 so that an air freshener cartridge can be loaded into (or removed from) the front cartridge slot 292 or rear cartridge slot 293. The outer peripheral sidewall 270 of front section 222 is provided with a radially extending flange 295 at a front end to serve as a stop feature or abutment that limits the outward travel of air freshener holder 280 and prevents the air freshener holder 280 from being accidentally pulled completely out of air freshener module 200.

The air freshener holder 280 is provided with various openings to facilitate the passage of airflow through the air freshener holder 280 and the air freshener cartridge housed in the air freshener holder 280. The airflow occurs successively through the rear panel 286, the mid panel 284, and the front panel 282. In particular, in order to facilitate the communication of air through the air freshener holder 280, the rear panel 286 is provided with an opening 247; the mid panel 284 is provided with a set of slits or openings 246; and the front panel 282 is provided with a set of slits or openings 245. Any type or arrangement of slits or openings can be used.

During operation, the air freshener holder 280 is located within the cavity 260 of the front section 222. The odorizing of the incoming airflow 114 occurs in a similar manner to the operation of the air freshener module 100 of FIGS. 1 through 5.

The above-described embodiments are merely exemplary illustrations of implementations set forth for a clear understanding of the principles of the invention. Many variations, combinations, modifications or equivalents may be substituted for elements thereof without departing from the scope of the invention. Therefore, it is intended that the invention not be limited to the particular embodiments disclosed as the best mode contemplated for carrying out this invention, but that the invention will include all the embodiments falling within the scope of the appended claims.

What is claimed is:

1. An air freshener module comprising:
   a hollow body housed rearward of a vehicle dashboard, the body having at least opposing sidewalls, an interior space, an air inlet at a rear of said body and an air outlet at the front of said body, wherein the air inlet is connected to and in fluid communication with a vehicle air duct, and said interior space defines an air passageway extending between said air inlet and said air outlet;
   at least one valve carried by the body and configured to control the passage of air through the air passageway between said air inlet and said air outlet, wherein said at least one valve comprises a throttle plate disposed in said air passageway proximate to said air inlet and selectively pivotal with respect to said body between an open position and a closed position; and
   a receptacle carried by the body and selectively removable from said body, the receptacle having a front panel, a rear panel, and a mid panel interposed between said front panel and said rear panel, said mid panel substantially parallel to said front panel and defining in combination with said front panel and said rear panel a front compartment and a rear compartment for holding an air freshener element, wherein said receptacle is pivotal with respect to said body about an axis substantially parallel to and substantially at a bottom edge of said front panel, wherein said receptacle is disposed at said air outlet and movable with respect to said body between an open position in which the receptacle and the front and rear compartments extend frontward of the vehicle dashboard providing access to said front compartment and said rear compartment of said receptacle from in front of said vehicle dashboard, and a closed position in which the receptacle and the front and rear compartments are housed within the interior space of the body and rearward of the vehicle dashboard and access to said front compartment and said rear compartment of said receptacle from in front of said vehicle dashboard is obstructed.

2. The air freshener module of claim 1, wherein said receptacle defines a plurality of openings therethrough for permitting the flow of air therethrough from said air passageway to outside said body when said receptacle is in said closed position.

3. The air freshener module of claim 1, wherein said front compartment is smaller than said rear compartment.

4. The air freshener module of claim 1, wherein a top edge of said mid panel is more proximate to said front panel than to said rear panel.

5. The air freshener module of claim 1, wherein said receptacle is detachable from and reattachable to said body.

6. The air freshener module of claim 1, wherein said throttle plate pivots about an axis substantially orthogonal to a longitudinal axis of said air passageway.

7. The air freshener module of claim 1, further including a user control switch operably connected to said at least one valve for selectively moving said at least one valve between said open position and said closed position.

* * * * *